(12) United States Patent
Ikeguchi et al.

(10) Patent No.: US 7,752,057 B2
(45) Date of Patent: Jul. 6, 2010

(54) SYSTEM AND METHOD FOR CONTINUOUS DATA ANALYSIS OF AN ONGOING CLINICAL TRIAL

(75) Inventors: Edward F. Ikeguchi, Larchmont, NY (US); Glen M. Devries, New York, NY (US); Tarek A. Sherif, New York, NY (US); Edwin Goodman, New York, NY (US)

(73) Assignee: Medidata Solutions, Inc., New York, NY (US)

( * ) Notice: Subject to any disclaimer, the term of this patent is extended or adjusted under 35 U.S.C. 154(b) by 0 days.

(21) Appl. No.: 11/810,483

(22) Filed: Jun. 6, 2007

(65) Prior Publication Data

US 2008/0046469 A1 Feb. 21, 2008

Related U.S. Application Data

(63) Continuation-in-part of application No. 10/667,848, filed on Sep. 22, 2003.

(51) Int. Cl.
*G06Q 10/00* (2006.01)
(52) U.S. Cl. .............................. 705/2; 705/3; 600/300; 600/301
(58) Field of Classification Search ................. 600/510, 600/300, 301; 705/2–4
See application file for complete search history.

(56) References Cited

U.S. PATENT DOCUMENTS

| 5,687,722 | A | 11/1997 | Tien et al. | |
|---|---|---|---|---|
| 5,757,664 | A | 5/1998 | Rogers et al. | |
| 5,924,073 | A | 7/1999 | Tyuluman et al. | |
| 5,978,751 | A | * 11/1999 | Pence et al. | 702/179 |
| 6,368,284 | B1 | 4/2002 | Bardy | |
| 6,398,728 | B1 | 6/2002 | Bardy | |
| 6,411,840 | B1 | 6/2002 | Bardy | |
| 6,418,334 | B1 | 7/2002 | Unger et al. | |

(Continued)

OTHER PUBLICATIONS

Vandeneugden et al., "Applying Concepts of Generalizability Theory on Clinical Trial Data to Investigate Sources of Variation and Their Impact on Reliability," Biometrics, 61, 295-304 (Mar. 2005).

(Continued)

*Primary Examiner*—Gerald J. O'Connor
*Assistant Examiner*—Rajiv J Raj
(74) *Attorney, Agent, or Firm*—Hoffman & Baron, LLP

(57) ABSTRACT

System and method of continuously analyzing trial data of an ongoing clinical trial is provided. A statistical analysis is performed on a trial database containing subject trial data without suspending the ongoing clinical trial. If the result of the statistical analysis does not exceed a predetermined threshold value, then the statistical analysis is repeated while the clinical trial is ongoing. In a blinded clinical trial, a grouped database is generated from the trial database and a blinding database prior to performing the statistical analysis. The grouped database groups the subject trial data according to the study groups. The ability to continuously monitor and analyze the trial data for statistical significance in tandem with data collection while the trial is ongoing provides many benefits to the researchers because the trial database no longer becomes the bottleneck in obtaining useful results and statistical analysis can be conducted on a near real-time basis without having to wait until completion of the trial.

41 Claims, 8 Drawing Sheets

U.S. PATENT DOCUMENTS

| | | | |
|---|---|---|---|
| 6,572,556 | B2 | 6/2003 | Stoycos et al. |
| 6,575,901 | B2 | 6/2003 | Stoycos et al. |
| 6,795,793 | B2 | 9/2004 | Shayegan et al. |
| 6,820,235 | B1 | 11/2004 | Bleicher et al. |
| 6,829,623 | B2 | 12/2004 | Tsuchida et al. |
| 6,832,110 | B2 | 12/2004 | Sohmer et al. |
| 6,834,256 | B2 | 12/2004 | House et al. |
| 6,904,434 | B1 | 6/2005 | Wallach et al. |
| 6,908,437 | B2 | 6/2005 | Bardy |
| 6,922,654 | B2 | 7/2005 | Krebs et al. |
| 7,054,823 | B1 | 5/2006 | Briegs et al. |
| 7,089,247 | B2 | 8/2006 | Kloos et al. |
| 2002/0099302 | A1* | 7/2002 | Bardy .................. 600/510 |
| 2002/0143577 | A1 | 10/2002 | Shiffman et al. |
| 2002/0183965 | A1 | 12/2002 | Gogolak |
| 2003/0065535 | A1 | 4/2003 | Karlov et al. |
| 2003/0088365 | A1* | 5/2003 | Becker .................. 702/19 |
| 2003/0104453 | A1 | 6/2003 | Pickar et al. |
| 2003/0108938 | A1 | 6/2003 | Pickar et al. |
| 2004/0078228 | A1 | 4/2004 | Fitzgerald et al. |
| 2004/0133450 | A1 | 7/2004 | Foureaux et al. |
| 2004/0148195 | A1 | 7/2004 | Kalies |
| 2004/0243439 | A1 | 12/2004 | Huggard et al. |
| 2004/0243440 | A1 | 12/2004 | Narimatsu et al. |
| 2004/0243555 | A1 | 12/2004 | Bolsius et al. |
| 2005/0010451 | A1 | 1/2005 | Marks et al. |
| 2005/0038692 | A1 | 2/2005 | Kane et al. |
| 2005/0149852 | A1 | 7/2005 | Bleicher et al. |
| 2005/0149869 | A1 | 7/2005 | Kehr et al. |
| 2005/0182657 | A1 | 8/2005 | Abraham-Fuchs et al. |
| 2005/0182658 | A1 | 8/2005 | Abraham-Fuchs et al. |
| 2005/0182664 | A1 | 8/2005 | Abraham-Fuchs et al. |
| 2005/0228808 | A1 | 10/2005 | Mamou et al. |
| 2005/0234740 | A1 | 10/2005 | Krishnan et al. |
| 2005/0267782 | A1 | 12/2005 | Zahlmann et al. |
| 2006/0129326 | A1 | 6/2006 | Braconnier et al. |
| 2006/0143047 | A1 | 6/2006 | Briegs et al. |
| 2006/0178906 | A1 | 8/2006 | Kalle et al. |
| 2006/0184493 | A1 | 8/2006 | Shiffman et al. |
| 2006/0224326 | A1 | 10/2006 | St. Ores et al. |
| 2006/0229916 | A1 | 10/2006 | Michelson et al. |

OTHER PUBLICATIONS

Shankar et al., "Epoch: an Ontological Framework to Support Clinical Trials Management," Conference on Information and Knowledge Management, 23-32 (2006).

Rao et al., "Clinical and Financial Outcomes Analysis with Existing Hospital Patients Records," Conference on Knowledge Discovery in Data, 416-425 (2003).

Shankar et al., "A Knowledge-Based System for Managing Complex Clinical Trials," Computer-Based Medical Systems, 2006, CBMS 2006., 19th IEEE International Symposium, 270-278 (Jun. 22-23, 2006).

Traher et al., "Clinical Trial Remote Data Capture Client/Server Solution," Conference on Object Oriented Programming Systems Languages and Applications, 175-176 (2000).

Anderson et al., "Scientific Information Retrieval System: A New Approach to Research Data Management," User Services Conference, 209-212 (1977).

Leticia Delgado-Herrea et al., "A model for the interim analysis process: a case study," Controlled Clinical Trials, vol. 24, Feb. 2003, pp. 51-65.

D. L. Demets, et al., "The agonizing negative trend in monitoring of clinical trials," Dec. 4, 1999, Lancet the, Lancet Limited. London, GB pp. 1983-1988.

Thomas R. Fleming, et al., "Monitoring of clinical trails: Issues and Recommendations," Controlled Clinical Trials, vol. 14, 1993, pp. 183-197.

* cited by examiner

40 ↘

| Subject ID | Study Arm |
|---|---|
| 101 | A |
| 102 | A |
| 103 | B |
| 104 | A |
| 105 | B |
| 106 | A |
| 107 | B |
| 108 | B |
| 109 | B |
| 110 | A |
| 111 | B |
| 112 | A |
| 113 | A |
| 114 | A |
| 115 | B |
| 116 | A |
| 117 | B |
| 118 | A |
| 119 | B |
| 120 | B |
| 121 | B |
| 122 | A |
| 123 | B |
| 124 | A |
| 125 | A |

| Subject ID | Heart Attack? 0=No 1=Yes |
|---|---|
| 101 | 0 |
| 102 | 1 |
| 103 | 1 |
| 104 | 0 |
| 105 | 1 |
| 106 | 0 |
| 107 | 1 |
| 108 | 0 |
| 109 | 0 |
| 110 | 0 |
| 111 | 1 |
| 112 | 0 |
| 113 | 0 |
| 114 | 1 |
| 115 | 1 |
| 116 | 0 |
| 117 | 1 |
| 118 | 0 |
| 119 | 1 |
| 120 | 1 |
| 121 | 0 |
| 122 | 0 |
| 123 | 1 |
| 124 | 0 |
| 125 | 0 |

| Subject ID | Study Arm | Heart Attack? 0=No 1=Yes |
|---|---|---|
| 101 | A | 0 |
| 102 | A | 1 |
| 103 | B | 1 |
| 104 | A | 0 |
| 105 | B | 1 |
| 106 | A | 0 |
| 107 | B | 1 |
| 108 | B | 0 |
| 109 | B | 0 |
| 110 | A | 0 |
| 111 | B | 1 |
| 112 | A | 0 |
| 113 | A | 0 |
| 114 | A | 1 |
| 115 | B | 1 |
| 116 | A | 0 |
| 117 | B | 1 |
| 118 | A | 0 |
| 119 | B | 1 |
| 120 | B | 1 |
| 121 | B | 0 |
| 122 | A | 0 |
| 123 | B | 1 |
| 124 | A | 0 |
| 125 | A | 0 |

| Subject ID | Data Status | Heart Attack? 0=No 1=Yes |
|---|---|---|
| 101 | 1 | 0 |
| 102 | 5 | 1 |
| 103 | 5 | 1 |
| 104 | 4 | 0 |
| 105 | 5 | 1 |
| 106 | 5 | 0 |
| 107 | 1 | Y |
| 108 | 5 | 0 |
| 109 | 5 | 0 |
| 110 | 4 | 0 |
| 111 | 5 | 1 |
| 112 | 3 | 0 |
| 113 | 5 | 0 |
| 114 | 1 | Still Evaluating Patient for Heart Attack |
| 115 | 5 | 1 |
| 116 | 5 | 0 |
| 117 | 5 | 1 |
| 118 | 1 | Don't Know |
| 119 | 5 | 1 |
| 120 | 5 | 1 |
| 121 | 5 | 0 |
| 122 | 4 | 0 |
| 123 | 3 | 1 |
| 124 | 5 | 0 |
| 125 | 5 | 0 |

| Key | |
|---|---|
| 1 | Queries Open |
| 2 | Pending Review |
| 3 | Pending SDV |
| 4 | Pending Lock |
| 5 | Locked |

| Subject ID | Data Status | Heart Attack? 0=No 1=Yes |
|---|---|---|
| 102 | 5 | 1 |
| 103 | 5 | 1 |
| 104 | 4 | 0 |
| 105 | 5 | 1 |
| 106 | 5 | 0 |
| 108 | 5 | 0 |
| 109 | 5 | 0 |
| 110 | 4 | 0 |
| 111 | 5 | 1 |
| 112 | 3 | 0 |
| 113 | 5 | 0 |
| 115 | 5 | 1 |
| 116 | 5 | 0 |
| 117 | 5 | 1 |
| 119 | 5 | 1 |
| 120 | 5 | 1 |
| 121 | 5 | 0 |
| 122 | 4 | 0 |
| 123 | 3 | 1 |
| 124 | 5 | 0 |
| 125 | 5 | 0 |

| | Key |
|---|---|
| 1 | Queries Open |
| 2 | Pending Review |
| 3 | Pending SDV |
| 4 | Pending Lock |
| 5 | Locked |

| Study Arm A |
|---|
| 0 |
| 1 |
| 0 |
| 0 |
| 0 |
| 0 |
| 0 |
| 1 |
| 0 |
| 0 |
| 0 |
| 0 |
| 0 |

66

| Study Arm B |
|---|
| 1 |
| 1 |
| 1 |
| 0 |
| 0 |
| 1 |
| 1 |
| 1 |
| 1 |
| 1 |
| 0 |
| 1 |

SYSTEM AND METHOD FOR CONTINUOUS DATA ANALYSIS OF AN ONGOING CLINICAL TRIAL

RELATED APPLICATION

This application is a continuation-in-part application of U.S. application Ser. No. 10/667,848 filed Sep. 22, 2003, which is incorporated herein by reference in its entirety.

TECHNICAL FIELD OF THE INVENTION

This application relates to data processing of clinical trial data and more specifically a system and method for statistically analyzing the clinical trial data.

BACKGROUND OF THE INVENTION

In the United States, the Food and Drug Administration (FDA) oversees the protection of consumers exposed to health-related products ranging from food, cosmetics, drugs, gene therapies, and medical devices. Under the FDA guidance, clinical trials are performed to test the safety and efficacy of new drugs, medical devices or other treatments to ultimately ascertain whether or not a new medical therapy is appropriate for widespread human consumption.

More specifically, once a new drug or medical device has undergone studies in animals, and results appear favorable, it can be studied in humans. Before human testing is begun, findings of animal studies are reported to the FDA to obtain approval to do so. This report to the FDA is called an application for an Investigational New Drug (IND).

The process of experimentation is referred to as a clinical trial, which involves four phases. In Phase I, a few research participants, referred to as subjects, (approximately 5 to 10) are used to determine toxicity of a new treatment. In Phase II, more subjects (10-20) are used to determine efficacy and further ascertain safety. Doses are stratified to try to gain information about the optimal portion. A treatment may be compared to either a placebo or another existing therapy. In Phase III, efficacy is determined. For this phase, more subjects on the order of hundreds to thousands of patients are needed to perform a meaningful statistical analysis. A treatment may be compared to either a placebo or another existing therapy. In Phase IV (post-approval study), the treatment has already been approved by the FDA, but more testing is performed to evaluate long-term effects and to evaluate other indications.

During clinical trials, patients are seen at medical clinics and asked to participate in a clinical research project by their doctor, known as an investigator. After the patients sign an informed consent form, they are considered enrolled in the study, and are subsequently referred to as study subjects. A study sponsor, generally considered to be the company developing a new medical treatment and supporting the research, develops a study protocol. The study protocol is a document describing the reason for the experiment, the rationale for the number of subjects required, the methods used to study the subjects, and any other guidelines or rules for how the study is to be conducted. Prior to usage, the study protocol is reviewed and approved by an Institutional Review Board (IRB). An IRB serves as a peer review group, which evaluates a protocol to determine its scientific soundness and ethics for the protection of the subjects and investigator.

Subjects enrolled in a clinical study are stratified into groups that allow data to be assessed in a comparative fashion. In a common example, one study arm, known as a control group (or "control"), will use a placebo, whereby a pill containing no active chemical ingredient is administered. In doing so, comparisons can be made between subjects receiving actual medication versus placebo.

Subjects enrolled into a clinical study are assigned to a study arm in a random fashion, which is done to avoid biases that may occur in the selection of subjects for a trial. For example, a subject who is a particularly good candidate to respond to a new medication might be intentionally entered into the study arm to receive real medication and not a placebo. This could skew the data and outcome of the clinical trial to favor the medication under study, by the selection of subjects who are most likely to perform well with the medication. In instances where only one study group is present, randomization is not performed.

Blinding is a process by which the study arm assignment for subjects in a clinical trial is not revealed to the subject (single blind) or to both the subject and the investigator (double blind). This minimizes the risk of data bias. Virtually all randomized trials are blinded by definition. In instances where only one study group is present, blinding is not performed.

Generally, at the end of the trial, the database containing the completed trial data is shipped to a statistician for analysis. If particular occurrences, such as adverse events, are seen with an incidence that is greater in one group over another such that it exceeds the likelihood of pure chance alone, then it can be stated that statistical significance has been reached. Using statistical calculations, the comparative incidence of any given occurrence between groups can be described by a numeric value, referred to as a "p-value". A p-value of 1.0 indicates that there is a 100% likelihood that an incident occurred as the result of chance alone. Conversely, a p-value of 0.0 indicates that there is a 0% likelihood that an incident occurred as a result of chance alone. Generally, values of $p<0.05$ are considered to be "statistically significant", and values of $p<0.01$ are considered "highly statistically significant".

In some clinical trials, multiple study arms, or even a control group, may not be utilized. In such cases, only a single study group exists with all subjects receiving the same treatment. This is typically performed when historical data about the medical treatment, or a competing treatment is already known from prior clinical trials, and may be utilized for the purpose of making comparisons.

The creation of study arms, randomization, and blinding are techniques that are used in most clinical trials where scientific rigor is of high importance. However, these methods lead to several challenges, since they prevent the clinical trial sponsor from tracking key information related to safety and efficacy.

Regarding safety, the objective of any clinical trial is to document the safety of a new treatment. However, in clinical trials where randomization is conducted between two or more study arms, this can be determined only as a result of analyzing and comparing the safety parameters of one study group to another. Unfortunately, because the study arm assignments are blinded, there is no way to separate out subjects and their data into corresponding groups for purposes of performing comparisons while the trial is being conducted. Since many clinical trials may last for time periods extending for years, it is conceivable to have a treatment toxicity go unnoticed for prolonged periods without intervention.

Regarding efficacy, any clinical trial seeking to document efficacy will incorporate key variables that are followed during the course of the trial to draw the desired conclusion. In addition, studies will define certain outcomes, or endpoints, at which point a study subject is considered to have completed the protocol. These parameters, including both key variables and study endpoints, cannot be analyzed by comparison between study arms while the subjects are randomized and blinded. This poses potential problems in ethics and statistical analysis.

When new medications or other health-related treatments are of superior efficacy to anything else, it is ethical to allow usage of the treatment for those in imminent need, even prior to final government approval. Conversely, when available, it is considered unethical to withhold such treatments. For example, if a medication were to be identified that eradicated the Human Immunodeficiency Virus (HIV), it would be unethical to allow diseased patients to continue suffering and even die of the illness, while the medication was being clinically tested for purposes of government approval. Ideally, in such situations, identification of effective treatments should occur early in the project. Under these circumstances, non-treatment arms (i.e., those taking placebos) could be construed as unethical and should be eliminated. At present, when clinical trials are randomized and blinded, identification of a particularly effective treatment may not be realized until the entire clinical trial is completed.

Another related problem is statistical power. By definition, statistical power refers to the probability of a test appropriately rejecting the null hypothesis, or the chance of an experiment's outcome being the result of chance alone. Clinical research protocols are engineered to prove a certain hypothesis about a medical treatment's safety and efficacy, and disprove the null hypothesis. To do so, statistical power is required, which can be achieved by obtaining a large enough sample size of subjects in each study arm. When too few subjects are enrolled into the study arms, there is the risk of the study not accruing enough subjects to enable the null hypothesis to be rejected, and thus not reaching statistical significance. Because clinical trials that are randomized are blinded, the actual number of subjects distributed throughout study arms is not defined until the end of the project. Although this maintains data collection integrity, there are inherent inefficiencies in the system, regardless of the outcome.

In a case where the study data reaches statistical significance, as accrual of subjects continues, and data is received, an optimal time to close a clinical study would be at the very moment when statistical significance is achieved. While that moment may arrive earlier in the course of a clinical trial, there is no way of knowing this, and therefore time and money are lost. Moreover, study subjects are enrolled above and beyond what is needed to reach the goals of the study, thus placing human subjects under experimentation unnecessarily.

In a case where the study data nearly reaches statistical significance, while the study data falls short of statistical significance, there is reason to believe that this is due to a shortage of enrollment in the study. Frequently, to develop more supportive data, clinical trials will be extended. These "extension studies", however, can only begin after a full closure of the parent study, frequently requiring months to years before starting again.

In a case where the study data does not reach statistical significance, there is no trend toward significance, and there is little chance of reaching the desired conclusion. In that case, an optimal time to close a study is as early as possible once the conclusion can be established that the treatment under investigation does not work, and study data has little chance of reaching statistical significance (i.e., it is futile). In randomized and blinded clinical trials, this conclusion is difficult to arrive at until data analysis can be conducted. In these situations, time and money are lost. Moreover, an excess of human subjects are placed under study unnecessarily.

To mitigate some of the risks related to the conduct of randomized and blinded clinical trials, a Data Safety Monitoring Board (DSMB) may be formed at the beginning of each protocol. In general, a DSMB is recommended for clinical trials that involve a potentially serious outcome (e.g., death, heart attack, etc.), are randomized and blinded, and extend for prolonged periods of time. In addition, a DSMB is required for trials that are sponsored by the United States government, namely, the National Institute of Health (NIH).

A DSMB generally consists of members who are domain experts in the field of study, such as physicians, as well as bio-statisticians. It is important that DSMB members be separate from personnel of the sponsor organization, and financial disclosure for all members is performed to minimize conflicts of interest. Prior to start of a clinical trial, standard operating procedures are established for the DSMB, including the frequency of meetings, initiation of interim analyses, conduct during interim analyses and criteria for discontinuation of the clinical trial. As it relates to the safety of study subjects, DSMB functions to examine trends of adverse occurrences rather than investigate specific reports, which are generally left to each IRB responsible for the activities of any given investigator. That is, DSMB receives only a snapshot data of a clinical trial and not a continuous analysis of trial data as with the present invention. Additionally, if dangerous conditions/events (e.g., deaths of study patients) are detected then the clinical trial must be suspended/interrupted to perform data analysis of the clinical trial. Further, DSMB cannot determine whether such dangerous conditions exist with the control group taking the placebo or the study group taking the drug under study without suspending the clinical trial. That is, the snapshot data is not sufficient for DSMB to determine the cause of the dangerous condition. Accordingly, DSMB's specificity and sensitivity of detecting dangerous condition is very low because it cannot determine whether the dangerous condition is related to the drug under study. Therefore the present invention proceeds upon the desirability of resolving this problem by increasing the sensitivity to such dangerous conditions by performing continuous data analysis without interrupting the clinical trial.

A typical method of collecting and analyzing patient data is illustrated in the flow chart shown in FIG. 1. Patient data or charts 10 from the clinical trial are collected manually in paper forms. Using a technology called Electronic Data Capture (EDC) or Remote Data Entry (RDE), a computer (not shown) displays a Case Report Form (CRF) to a clinical research coordinator (CRC) 12, typically a nurse or doctor. The CRC 12 then enters the patient data 10 through the computer display which is received in block 14 by an EDC system which executes all of the steps included in a box 11. The received data is stored in a clinical trial database 38 through a link 20 which can be an electronic link such as a telephone line or Internet link. In block 18, it is determined whether the data inputted by the CRC 12 is clean using one or more rules. The rules may be implemented by simple range checking scripts, or by an inference rule engine or deterministic rule engine in order to identify potential problems with the data.

In addition to the software programs, block 18 may also involve research personnel known as monitors or Clinical Research Associates (CRA) who travels to the various research sites to perform source document verification (SDV) whereby the data in the database 38 is reconciled against individual patient charts to the degree required in the protocol.

If it is determined that the data entered is not clean, then block 22 generates a query which is then sent over the link 20 to the CRC 12. The blocks 14, 18 and 22 are repeated until all of the subject data 10 are entered. This is an iterative process that continues until resolution of all queries in the database 38.

Once all data 10 are entered, block 24 determines whether the clinical trial is over. If no, then the EDC system continues to receive the patient trial data 10 through block 14 as the trial continues. If the trial is over, control passes to block 26 where the entire database is locked from any changes, deletions or insertions of the data in the database 38. In one embodiment, locking involves turning the database 38 into a "read-only" state.

In block 28, a blinding data from a blinding database is retrieved. A simplified example blinding database 40 is shown in FIG. 4. The blinding database 40 is a database table having two columns. The first column contains a patient subject ID (subject identifier) and the second column contains an associated study arm or group the patient belongs to. In the table 40, 13 subjects belong to Study Arm "A" and 12 subjects belong to Study Arm "B". Because the database 40 is not associated with actual trial data, the table 40 by itself is relatively uninformative.

A simplified example trial database 38 is shown in FIG. 5. The embodiment shown is a database table containing two columns. The first column contains a patient subject ID and the second column is a database field called "Heart Attack" which specifies whether the subject had a heart attack. An entry of 0 means NO and entry of 1 means YES. As can be seen from the trial database 38, due to blinding of the subjects in the study groups, there is no way of knowing whether or not any discrepancy exists in the number of heart attacks seen in Group A versus B. Because the trial is randomized, without the blinding data 40, the table 38 by itself is relatively uninformative.

In block 28, an unblinded database is produced from the trial database 38 and the retrieved blinding database 40 in which the subject ID is used as a common key. The result of the unblinding process of block 28 is shown in FIG. 6 as the unblinded database 41. In the embodiment shown, one database table is produced. The table 41 contains subject identifiers, Study Arm of the subjects, and Heart Attack data of those subjects. As can be appreciated by a person of ordinary skill in the art, there is a direct traceability from study data and subject ID to Study Arm.

In block 30, statistical analysis is performed on the unblinded data 42 to find out the efficacy and safety of the completed clinical trial.

During the course of any given randomized and blinded clinical trial, an interim analysis may be conducted. An interim analysis may result from urging of the DSMB for cause, or be a pre-planned event as described in the study protocol.

Conducting an interim analysis involves a process where the available data is verified and cleaned. The clinical trial is typically interrupted or suspended to enable the available data to be verified and cleaned. The verification process generally involves a process by which trained personnel travel to the various research sites to reconcile submitted data against source documents, which generally implies the patient's chart, laboratory reports, radiographic readings, and others. The data cleaning process may involve a series of documented communications between the research site and a central data coordinating personnel to resolve inconsistencies or other conflicting data.

The refined database must then be sent to an impartial third party for statistical analysis. To conduct the analysis, the statistician must un-blind the clinical trial database by combining both the study data with the blinding key of which subjects are assigned to particular study arms. Since the clinical study is expected to continue beyond the interim analysis, the process of un-blinding must be conducted with great caution, so as not to reveal the blind status of subjects to any personnel involved in the execution of the clinical trial. Once a statistician has completed the interim analysis, a report is issued to the trial sponsor and DSMB.

Inclusive of the data cleaning, verification, un-blinding and statistical analysis processes, as well as the administrative resources for coordinating several groups of personnel for the un-blinding process, an interim analysis is often arduous, time-consuming and expensive.

In spite of the latest technological advancements made in the area of data collection through electronic systems, there is still a disadvantage in that it is very difficult to draw conclusions about a medical treatment while the data is being collected during the trial. This limitation stems primarily from the fact that statistical analysis cannot begin until the trial data has been fully cleaned and processed. At present, statistical analysis can only be conducted upon data in an "en bloc" fashion. This creates a situation where the ability to draw conclusions about a medical therapy inevitably lags behind the process of simply obtaining data in a database.

Regardless of how efficient the data collection process may be made through automation, the ability to acquire the information needed for critical decision-making is still suspended by the requirement to obtain a locked database in order for statistical work to advance.

Therefore, it is desirable to provide a method and system for conducting data analysis, i.e., statistical analysis, on the clinical data collected while the clinical trial is ongoing. This advantageously permits the present invention to identify positive or negative conditions/events/trends much more rapidly than possible with currently available systems and methods.

In the case of a randomized clinical trial where maintaining confidentiality is important, it is also desirable to provide a secure system in which the blinding information is integrated in such a way that the clinical trial data and blinding data are stored securely to prevent users from accessing the data and yet allow the execution of programs for performing statistical comparisons between study arms while the clinical trial is ongoing.

SUMMARY OF THE INVENTION

It is an object of the present invention to provide a system and method for continuously analyzing trial data of an ongoing clinical trial.

Another object of the present invention is to provide the system and method as aforesaid which analyzes the trial data without interrupting or suspending the ongoing clinical trial.

A further object of the present invention is to provide the system and method as aforesaid which performs statistical analysis on the trial data and repeatedly performs such statistical analysis until the result of such statistical analysis or the rate of change in a predetermined statistical parameter exceeds a predetermined threshold.

In accordance with an embodiment of the present invention, the system and method continuously analyzes trial data of an ongoing clinical trial. The system and method accesses the subject trial data from a trial database and performs statistical analysis on the accessed trial data. The system and method repeatedly performs the statistical analysis while the clinical trial is on going if it determines that result of the statistical analysis or the rate of change of the statistical parameter does not exceed a predetermined threshold value.

In accordance with an exemplary embodiment of the present invention, a method of continuously analyzing trial data of an ongoing clinical trial, comprises the steps of: accessing a trial database comprising trial data of subjects in the ongoing clinical trial; performing statistical analysis on the trial data to determine a parameter of statistical significance without suspending the ongoing clinical trial, determining whether the result of the statistical analysis exceeds a threshold value, and repeating the steps of accessing, performing and determining during the ongoing clinical trial if it is determined that the results of the statistical analysis does not exceed the threshold value.

In accordance with an exemplary embodiment of the present invention, a computer readable media comprising a code for continuously analyzing trial data of an ongoing clinical trial. The code comprises instructions for accessing a trial database comprising trial data of subjects in the ongoing clinical trial, performing statistical analysis on the trial data to determine a parameter of statistical significance without suspending the ongoing clinical trial, determining whether the result of the statistical analysis exceeds a threshold value, and repeating the steps of accessing, performing and determining during the ongoing clinical trial if it is determined that the result of the statistical analysis does not exceed the threshold value.

In accordance with an exemplary embodiment of the present invention, a system a for continuously analyzing trial data of an ongoing clinical trial comprises a trial database comprising trial data of subjects in the ongoing clinical trial and a processor. The processor performs statistical analysis on the trial data to determine a parameter of statistical significance without suspending the ongoing clinical trial and determines whether the result of the statistical analysis exceeds a threshold value. The processor is operable to repeatedly access, perform and determine during the ongoing clinical trial if it is determined that the result of the statistical analysis does not exceed the threshold value.

In accordance with an embodiment of the present invention, the system and method uses a user definable criteria that defines the level of cleanliness of subject data for statistical analysis. In that case, only those subject data that meet the user defined criteria are selected from the trial database for statistical analysis.

In accordance with an embodiment of the present invention, the system and method uses a rate of change for a given statistical parameter. The rate of change may be a user definable criteria including the parameter to be measured and the time interval through which the parameter has changed.

In accordance with an embodiment of the present invention, the system and method uses a value for the degree of disparity in any given statistical evaluation between two groups of a multi-arm clinical study. The value for the degree of disparity may be a user definable criteria including the parameter to be measured.

In accordance with an embodiment of the present invention, the system and method waits for a predetermined time period before repeating the statistical analysis if the result of the statistical analysis does not exceed the threshold value. This is done so additional subject data can be collected and added to the trial database.

In accordance with an embodiment of the present invention, the clinical trial is blinded. Accordingly, the system and method of the present invention accesses a blinding database in addition to the trial database to obtain additional information, such as subject identifiers and associated study group identifiers. Each study group identifier identifies which study group a particular subject belongs to. The system and method of the present invention generates a grouped database from the clinical database and the blinding database for statistical analysis in which the trial data is grouped according to the subject's study group. Preferably, the system and method generates a data table for each study group and contains trial data associated with all of the subjects that belong to that study group.

In accordance with an embodiment of the invention, the system and method stores the unblinded database in a memory device that is inaccessible by any user in order to preserve the blindness of the clinical trial. The unblinded database is physically part of the trial database and/or electronic data collection (EDC) system of the present invention, but logically separated by user access-permission. Alternatively, the unblended database can be physically separate from the trial database.

In accordance with an embodiment of the invention, the system and method performs the statistical analysis without locking the trial database.

In accordance with an embodiment of the invention, if the result of the statistical analysis or the rate of change of a statistical parameter exceeds the threshold value, a user is alerted. The predetermined threshold value may include a predetermined statistical significance value or a rate of change.

In accordance with an embodiment of the invention, the system and method offers many statistical models to users to choose from. The system and method retrieves and runs a user selected statistical model on the clinical trial database.

In accordance with an embodiment of the invention, the system and method graphically presents the statistical parameters and their trends over time to end-users with the correct permission level.

In accordance with an embodiment of the present invention, the system and method enables the user to adjust the distribution of the subjects within the blinding table for future enrollees to be grouped in a particular manner.

Various other objects, advantages, and features of the present invention will become readily apparent from the ensuing detailed description, and the novel features will be particularly pointed out in the appended claims.

BRIEF DESCRIPTION OF THE DRAWINGS

The following detailed description, given by way of example, and not intended to limit the present invention solely thereto, will best be understood in conjunction with the accompanying drawings in which:

FIG. 4 is an example of a blinding database;

FIG. 5 is an example of a trial database containing subject trial data;

FIG. 6 is an example of an unblinded database derived from the blinding database of FIG. 4 and the trial database of FIG. 5 in accordance with an exemplary embodiment of the present invention;

FIG. 7A is an example of a trial database containing a status field that represents the levels of cleanliness of the subject data records in accordance with an exemplary embodiment of the present invention;

FIG. 7B is a filtered trial database containing a subset of the trial database of FIG. 7A which have been selected as a function of a user specified status in accordance with an exemplary embodiment of the present invention; and FIG. 8 is an example of a grouped database derived from the blinding database of FIG. 4 and the filtered trial database of FIG. 7B in accordance with an exemplary embodiment of the present invention.

DETAILED DESCRIPTION OF THE EMBODIMENTS

The present application is applicable to any clinical studies utilizing electronic data collection, including but not limited to collecting clinical data over a network from a plurality of trial participants. Clinical studies can involve multiple groups to enable comparisons to be made between subjects receiving the actual medication versus placebo. Also, clinical studies can involve a single study group, wherein data collected from the clinical trial can be compared to data from other similar clinical trials or studies, or to historical data. Although randomization or randomized studies lend themselves to clinical trials with multiple study groups, it is not necessary for clinical trials with single study group. It is appreciated that randomization is not necessary required for clinical trials with multiple study groups, the study subjects can request assignment to a particular study group or arm, or can be assigned to a particular study group at the discretion of the investigator.

Most clinical trials utilize multiple study arms, randomization, and blinding so they can maintain scientific rigor and conform to requirements of FDA approval for a new drug and/or new treatment. However, these rigorous clinical trials can lead to several challenges, since they prevent the clinical trial sponsor from tracking key information related to safety and efficacy while the clinical trial is ongoing. Such analysis and comparisons are not possible with the prior art systems and methods until the clinical trials have ended or unless the clinical trials are interrupted/suspended. That is, it is conceivable that a potential positive or negative effects of a drug under study will go unnoticed until the clinical trial is completed. The present invention proceeds upon desirability of making such positive or negative information available while the clinical trial is ongoing and without interrupting the clinical trial.

Even in non-randomized, single arm, and unblinded clinical studies, little if any statistical conclusion can be drawn until after the trial database comprising the trial data can be cleaned of errors and locked. Current operational methods call for paper forms that are filled out by investigators and later keyed into a database. This latter activity may lag behind the paper forms for many days to weeks, ultimately compounding the delays seen in a clinical trial that may involve hundreds of thousands of forms. The delay in transforming data from a paper form to an electronic format further delays the analysis of clinical study data because data cleaning operation cannot start until the data is in electronic format. The present invention resolves these issues by performing these data analysis on trial data while the clinical trial is ongoing and without interrupting the clinical trial.

Figure 2:
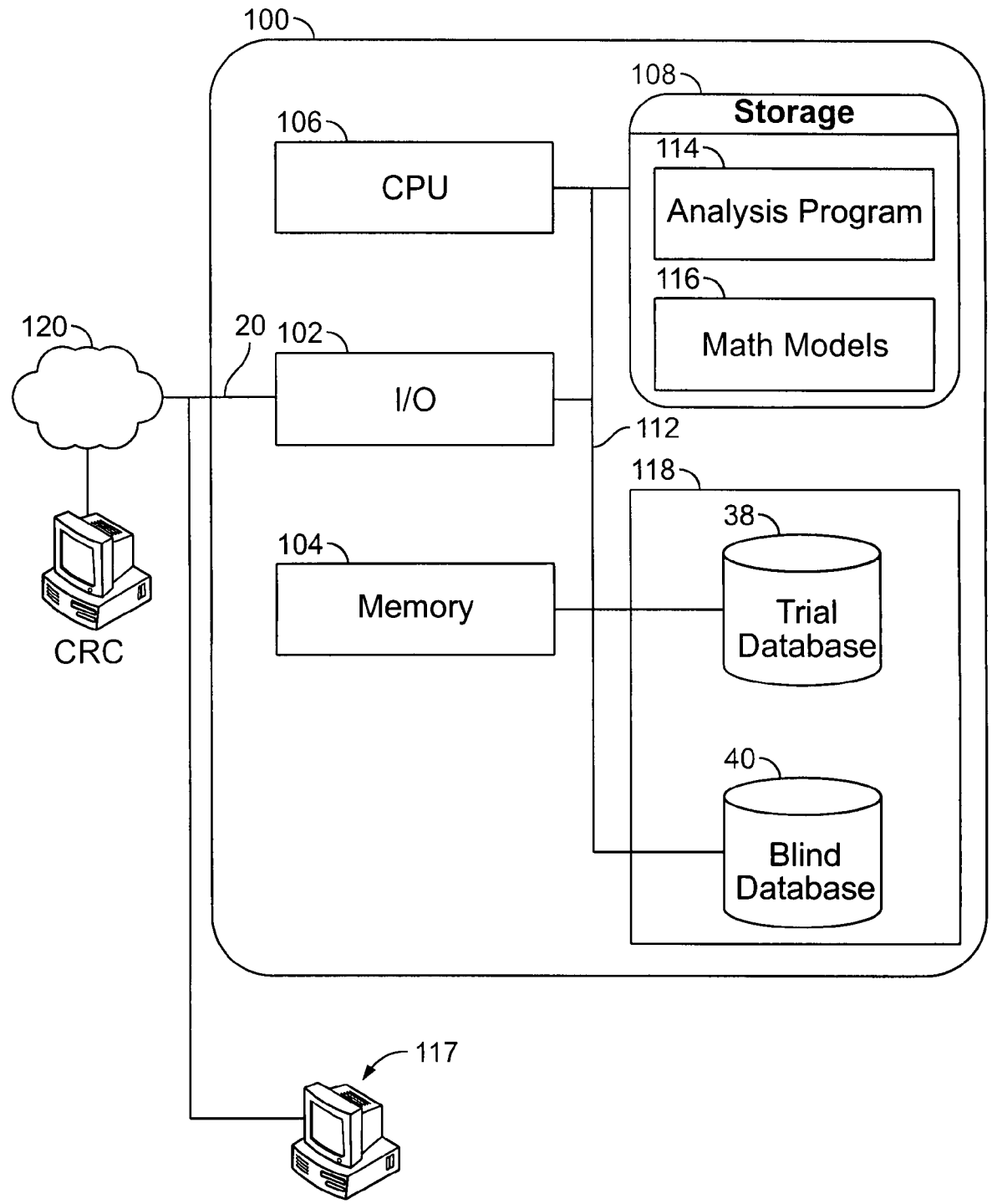
FIG. 2 is a functional block diagram of a clinical trial management system in accordance with an exemplary embodiment of the present invention.

Turning now to FIG. 2, there is shown a clinical trial data management system 100 in accordance with an exemplary embodiment of the present invention which is an Internet-enabled application solution framework that automates data collection, data cleaning, grouping if needed (as will be explained more fully later herein) and statistical data analysis while the trial is ongoing. The system 100 is connected to a computer network such as the Internet 120 through, for example, an I/O interface 102, which receives information from and sends information to Internet users over a communication link 20 and to one or more operators using a work station 117. The Internet users are typically clinical research coordinators (CRC's) located at various trial sites who transcribe the subjects' charts to the system 100. The system 100 comprises, for example, memory 104 which is volatile, processor (CPU) 106, program storage 108, and data storage device 118, all commonly connected to each other through a bus 112. The program storage 108 stores, among others, a clinical trial analysis program or module 114 and one or more mathematical models 116 that are used to analyze the subject data and obtain the p-value for statistical significance. The data storage device 118 stores a clinical trial database 38 and blinding database 40. An example of a clinical trial database 38 is shown in FIG. 5 and an example of a blinding database 40 is shown in FIG. 4. The clinical trial database 38 and the blinding database 40 can be separated either physically or logically through user access-permission. The blinding database 40 can be accessed manually by permitted users or by the system 100 to establish grouping assignments for upcoming or future enrollment into the clinical trial. It is appreciated that some clinical studies are performed without the use of blinding. In such instances, the system does not utilize the blinding database 40 because the study patients and or their investigators are informed of what therapy is being received and or administered respectively. Any of the software program modules in the program storage 108 and data from the data storage 110 are transferred to the memory 104 as needed and is executed by the processor 106.

The system 100 can be any computer such as a WINDOWS-based or UNIX-based personal computer, server, workstation, minicomputer or a mainframe, or a combination thereof. While the system 100 is illustrated as a single computer unit for purposes of clarity, persons of ordinary skill in the art will appreciate that the system may comprise a group of computers which can be scaled depending on the processing load and database size.

Figure 1:
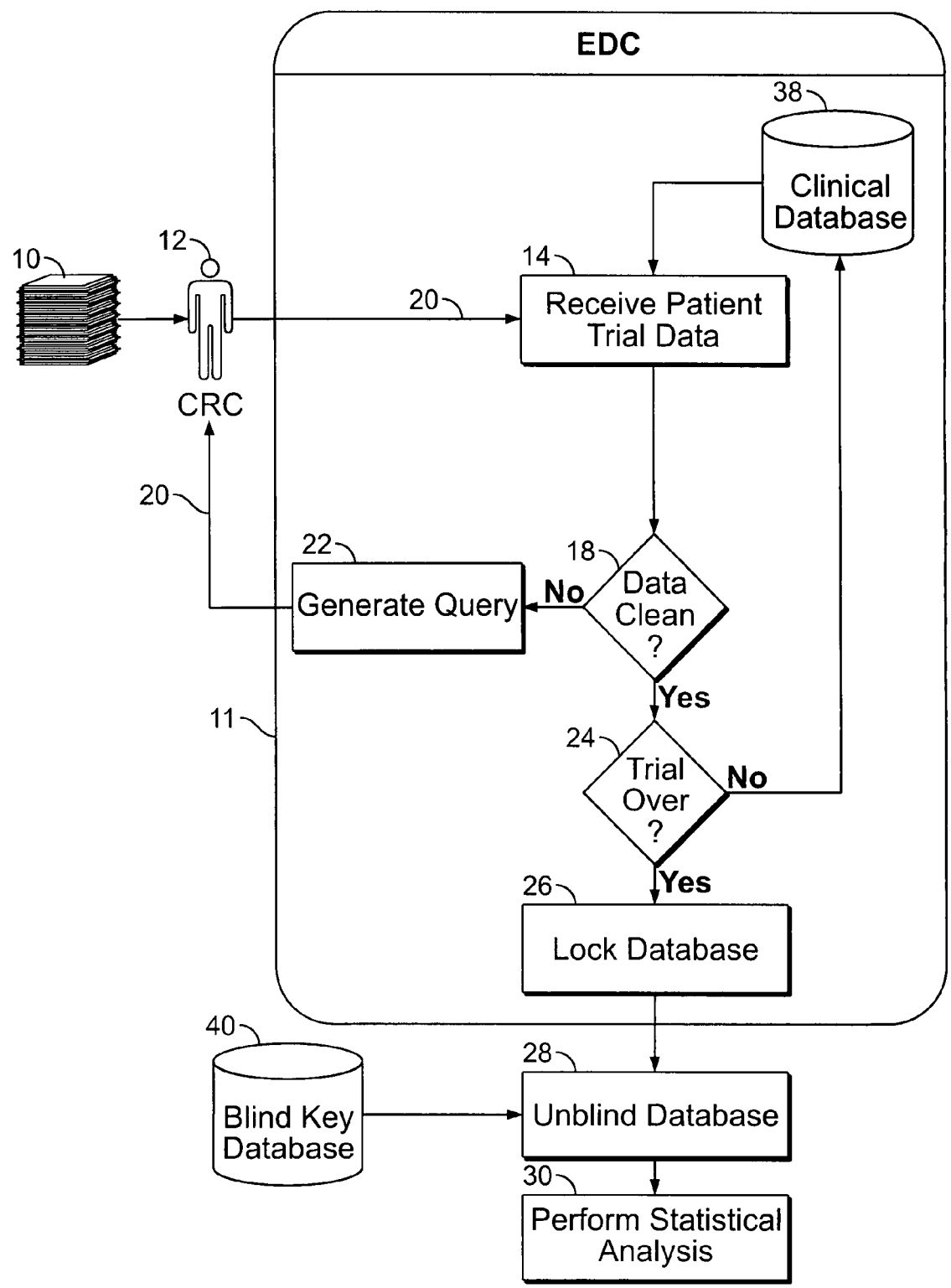
FIG. 1 is a flow diagram of a method of collecting and analyzing clinical trial data using an EDC system.
Figure 3:
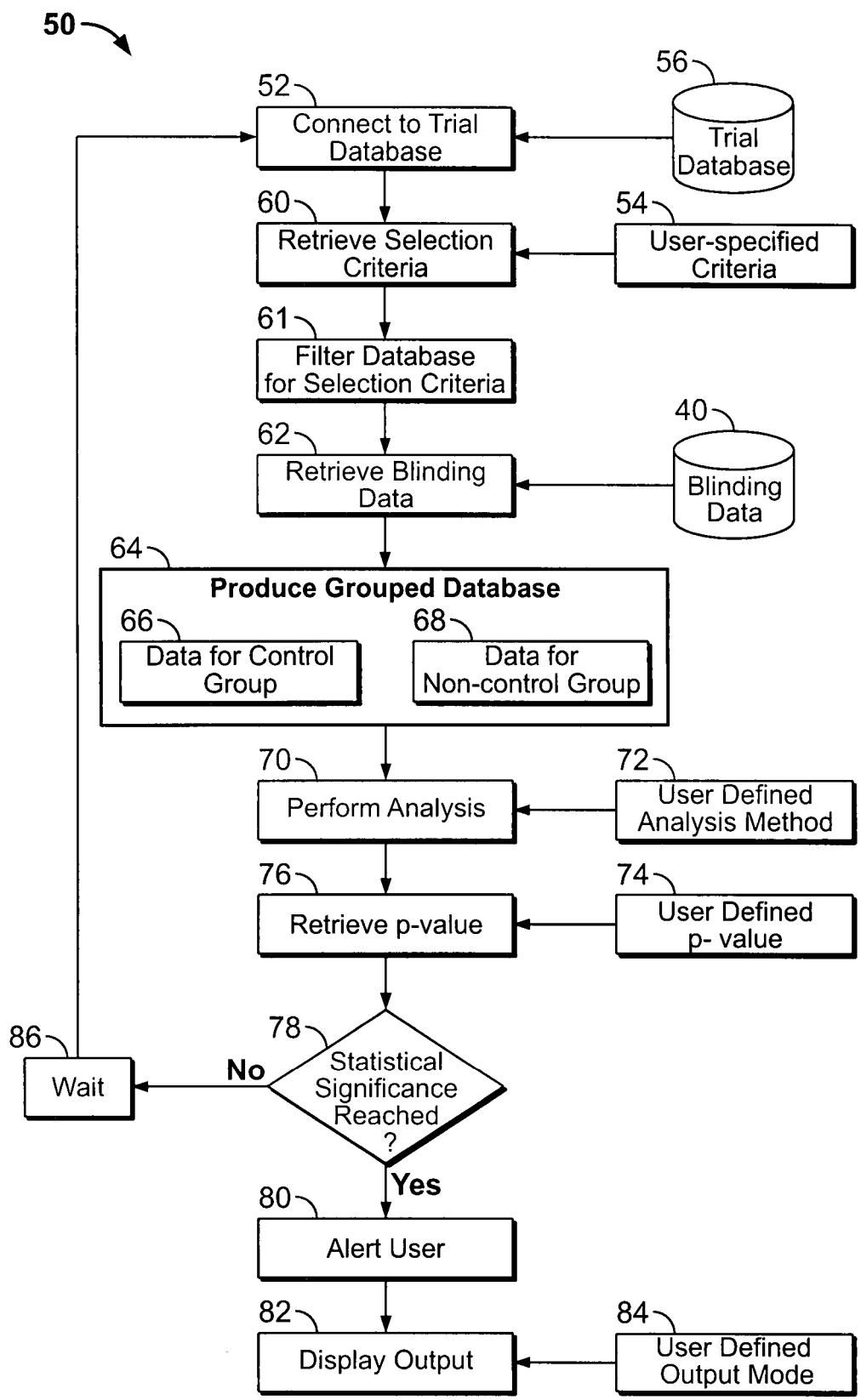
FIG. 3 is a flow diagram of a software routine that continuously analyzes the trial data while the clinical trial is ongoing in accordance with an exemplary embodiment of the present invention.

FIG. 3 illustrates a flow diagram of a software routine 50 that continuously analyzes the trial data while the trial is ongoing in accordance with an exemplary embodiment of the present invention. The routine 50 is stored in the storage device 108 and works with the EDC system 11 of FIG. 1 while the system 11 continuously collects and cleans the trial data in accordance with an exemplary embodiment of the present invention.

The routine 50 connects to a trial database 56 through a log-in procedure at block or step 52. A simplified exemplary trial database 56 is shown in FIG. 7A. The trial database 56 contains three columns comprising a patient subject ID field, a data status field, which specifies the level of cleanliness, and a "Heart Attack" field similar to FIG. 5.

FIG. 7A illustrates simplified trial data records that are at different levels of cleanliness. In the example shown in FIG. 7A, there are five levels of status. Level 1 indicates that there is an outstanding query that needs to be answered by the CRC 12 (see step 22 in FIG. 1). Level 2 indicates that the record is pending a review by another reviewer such as the sponsor of the trial. Level 3 indicates that it is pending a review by a clinical research associate (CRA) to travel to a research site to perform what is known as a source document verification (SDV). This typically involves a verification of the trial record with an actual patient chart. Level 4 indicates that it is pending a lock barring any intervention by any reviewer. Finally, Level 5 indicates that the record is locked which represents the highest level of clean data.

In the "Heart Attack" field, an entry of 0 means NO and entry of 1 means YES. The "Heart Attack" field also includes some erroneous data such as "don't know" for subject 118 or "Y" for subject 107. Accordingly, the status for those records indicates a "1" in which queries are outstanding.

Once connected, the routine 50 retrieves a user specified criteria 54 stored in the storage device 108 which specifies the status or level of cleanliness of the trial database at step 60 and retrieves the trial database 56 which is filtered for those database records that satisfy the retrieved criteria at step 61. For an example, if the retrieved user specified criteria is 3, the routine 50 selects only those records that have a status of 3 or better at step 61 Such a filtered database 58 is shown in FIG. 7B. While the database 58 has a relatively higher level of cleanliness, it does have a fewer number of records. This is useful since, at any given point in time during the data collection process, the clinical trial database 56 may have data that has any combination of data pending SDV, containing outstanding queries, completed SDV but awaiting lock, and so on. Depending upon the operating procedures defined for any such clinical trial, only certain subsets of data may be suitable for inclusion in an analysis.

Once the trial database 58 is filtered according to the user specified criteria at step 61, the routine 50 retrieves the blinding data, such as those exemplary blinding data shown in FIG. 4, from the blinding database 40 at step 62. The routine 50 utilizes the filtered trial database 58 and the blinding database 40 to produce a grouped database 42, such as exemplary shown in FIG. 8, at step 64. In accordance with an exemplary embodiment of the present invention, two database tables 66, 68, one for each study group without identifying subjects, are produced for example, as shown in FIG. 8. One table 66 groups the Heart Attack data of subjects that belong to a control group (Study Arm A) while the other table 68 groups the Heart Attack data of subjects that belong to a non-control group (Study Arm B). As can be appreciated by person of ordinary skill in the art, there is no way to trace the origins of any given data point in either table 66 or table 68, to its original subject, and therefore either table, by itself, is relatively uninformative. Taken together, however, note that there seems to be a lot more heart attacks occurring in Study Arm B.

Turning now to FIG. 3, there is illustrated a process of continuously analyzing trial data of an ongoing randomized clinical trial in accordance with an exemplary embodiment of the present invention. The system 100 maintains the clinical trial database 38 and the blinding database 40 as separate physical and digital entities, in order to maintain their distinct nature. Alternatively, the distinction between the two databases could be logical rather than physical, based upon user access-permission. In other words, the trial data and blind data remain as two separate data tables and no table is created containing all of the following information: the subject identifier, study group and heart attack status. Furthermore, system communication with the blinding database table occurs only by virtue of the machine programs of the present invention executing specified actions to sort the clinical trial data in accordance with an exemplary embodiment of the present invention. The clinical trial data is preferably segregated into generic pools of data and remains de-identified or unlinked to both the subject and the study arm, and thus indecipherable from the standpoint of the ability to trace a particular data item back to a specific subject.

The routine 50 retrieves a user defined analysis method 72 stored in the storage device 108 and retrieves the method from the mathematical models 116 stored in the storage device. The routine 50 of the present invention runs the model to analyze the grouped database 42 at step 70. Preferably, the routine 50 of the present system and method obtains a parameter of statistical significance, e.g., a p-value (a statistical significance of the safety and efficacy of the unblinded database 41) at step 76. An exemplary unblinded database 41 in accordance exemplary embodiment of the present invention is shown in FIG. 6. It is appreciated that the mathematical model can include one or more formulas, representing mathematical calculations, whereby one or more variables in the clinical trial database are identified, and numeric result can be obtained. Such formulas can include calculations of: mean, median, mode, range, average deviation, standard deviation, and variance. In addition, an administrator can enter mathematical formulas to further analyze the data to make comparisons between groups of data, as defined by the study arms, to determine statistical metrics and significance by methods including Chi-square analysis, t-test, f-test, one-tailed test, two-tailed test, and Analysis of Variance (ANOVA). In accordance with an aspect of the present invention, the system and method stores these calculated statistical values and associated time points, thereby allowing the present system and method to track trends, such as a rate of change.

Once the mathematical analysis is completed, the routine retrieves a user-defined p-value 74 stored in the storage device 108 at step 76. The routine 50 then determines whether the derived p-value exceeds the retrieved user defined p-value at step 78. As discussed in detail herein, a typical user defined p-value can be 0.05 indicating that the difference between the control group and non-control group is statistically significant. Thus, if the derived value is less than 0.05, then the inquiry at step 78 is answered in the affirmative and the routine 50 sends an alert to the user or operator without displaying the actual output value(s) at step 80. The alert can be in the form of a flashing display, alarm, a change in the system output display to the user by virtue of color-coding, fonts, icons or text, or an automated system generated message to the user by way of email, facsimile, telephone or pager.

Alternatively, in accordance with an exemplary embodiment of the present invention, the routine 50 can retrieve a user-defined rate of change value for a given statistical parameter at step 76. The value of the rate of change can be positive or negative number, or any indication of positivity or negativity in the rate of change. A negative rate of change in the p-value can indicate a lack of efficacy in a particular study arm, and the routine 50 can establish this negative rate of change in the p-value as a trigger for alerting the user or operator at step 78. Thus a negative rate of change in the p-value would result in the inquiry at step 78 being answered in the affirmative resulting in the routine 50 sending an alert to the user or operator at step 80.

In accordance with an exemplary embodiment of the present invention, the routine 50 retrieves a user-defined difference in a statistical value between two study arms of the clinical study at step 76. Such difference can signify a divergence in statistical trends between the study arms of a clinical study and the routine 50 can establish this difference in the statistical value as a trigger for alerting the user or operator at step 78. Thus if the degree of disparity between the two study arms of a clinical study exceeds a user-defined value, then the inquiry at step 78 is answered in the affirmative and the routine 50 sends an alert to the user or operator at step 80.

In accordance with an exemplary embodiment of the present invention, at step 82, the routine 50 can generate and display output in accordance with the user defined output mode 84, as the generic data tables 66, 68 generated at step 64. The output data can take various formats including plain text, American Standard Code for Information Interchange (ASCII), and SAS. Where appropriate, this allows the user to perform customized statistical analysis using the present invention to be performed. It is appreciated that these outputs can also be integrated with other software packages to generate customized graphical reports.

In accordance with an exemplary embodiment of the present invention, if the trial is a randomized clinical trial, then the routine 50 stops at step 80 and provides a Boolean output as to whether or not a particular study parameter has reached the desired level of statistical significance or not at step 80. The routine 50 skips step 82 or makes it available only to a select group of users based upon access-permission. It is appreciated that this functionality or accessibility can be determined by an administrative user as a configurable aspect of the present system and software. This advantageously maintains the blinding information as secure as possible, thereby minimizing any inference that can be made about the study arm of any given subject. In monitoring the exact numeric determination of statistical significance for any given clinical trial variable, it is conceivable that the accession of new data could cause statistical metrics for a particular study arm to change in such a manner that inference can be made regarding the blinding status of the subject whose data was most recently added, thus compromising statistical veil.

It is appreciated that even in non-randomized clinical trials, the display of specific numeric value corresponding to a parameter of statistical significance by the routine 50 at step 80 is useful and beneficial. Since there is no blinding information to protect in non-randomized clinical trials, the display of such parameter of statistical significance can be offered as a second mode of operation by the present invention. Alternatively, the present invention can provide a third mode of operation, whereby numeric ranges of statistical significance can be defined into groups that can be displayed to the user of the present invention.

However, if the derived p-value is higher than the user-defined p-value, the rate of change is positive or the degree of disparity between the study arms does not exceed the user defined threshold value, then the inquiry at step 78 is answered in the negative and the routine 50 proceeds to step 86. The routine 50 waits a predetermined time so additional clinical data is collected and stored in the clinical trial database 58 at step 86 and proceeds to step 52. The routine 50 then repeats the process of analyzing the trial data of an ongoing clinical trial. In other words, the system 100 is active throughout the data collection phase of the clinical trial, sending alerts when key parameters reach the pre-set or predetermined level of statistical measure or significance.

As can be appreciated by persons of ordinary skill in the art, the ability of the present clinical trial system 100 to continuously and confidentially monitor and analyze the trial data for statistical significance in tandem with data collection while the trial is ongoing is a tremendous benefit to the researchers. The trial database no longer becomes the bottleneck in obtaining useful results and statistical analysis can be conducted on a near real-time basis.

This continuous near real-time statistical analysis feature in turn has far reaching implications. Specifically, by providing researchers with an early indication of the clinical trial, the present invention shortens the time frame required to reach critical decisions about a new medical therapy. Still another advantage is that the present system improves patient safety by setting thresholds for triggering alerts for adverse events. A related advantage is that a futile trial can be ended early, thereby saving the substantial cost of conducting the trial. Conversely, for a successful medical treatment, a trial can be ended early or the placebo arm can be eliminated. Based upon statistical trends, the distribution of enrollees can be altered while the clinical trial is ongoing in order to adjust or better test the objectives of the clinical trial or scientific hypothesis. The present invention also provides the ability to more accurately identify the need to perform a full-scale interim analysis.

In accordance with an exemplary embodiment of the present invention, a computer readable media comprising a code for continuously analyzing trial data of an ongoing clinical trial. The code comprises instructions for accessing a trial database comprising trial data of subjects in the ongoing clinical trial, performing statistical analysis on a trial data of statistical significance without suspending the ongoing clinical trial, determining whether the result of the statistical analysis exceeds a threshold value, and repeating the steps of accessing, performing and determining during the ongoing clinical trial if it is determined that the result of the statistical analysis does not exceed the threshold value. Further the code comprises instructions for selecting only those subject data that meets the user defined criteria from the trial database for statistical analysis. The user defined criteria defining the level of cleanliness of the subject data for statistical analysis.

In accordance with an exemplary embodiment of the present invention, a system a for continuously analyzing trial data of an ongoing clinical trial comprises a trial database comprising trial data of subjects in said ongoing clinical trial and a processor. The processor performs statistical analysis on the trial data to determine a parameter of statistical significance without suspending the ongoing clinical trial and determines whether the result of the statistical analysis exceeds a threshold value. The processor is operable to repeatedly access, perform and determine during the ongoing clinical trial if it is determined that the result of the statistical analysis does not exceed the threshold value.

Various omissions, modifications, substitutions and changes in the forms and details of the device illustrated and in its operation can be made by those skilled in the art without departing in any way from the spirit of the present invention. Accordingly, the scope of the invention is not limited to the foregoing specification, but instead is given by the appended claims along with their full range of equivalents.

What is claimed is:

1. A computer readable storage medium comprising computer executable instructions for continuously analyzing trial data of an ongoing clinical trial that, when executed by a processor, cause the processer to:

access a trial database comprising trial data of subjects in a blinded ongoing clinical trial comprising a multi-arm study while maintaining blindness of said blinded ongoing clinical trial;

access a blinding database comprising subject identifiers and associated study group identifiers, wherein a subject's study group being identifiable by a study group identifier;

generate a grouped database from said trial database and said blinding database for statistical analysis, said grouped database grouping said trial data of said subjects based on their study group;

perform near real-time statistical analysis on said trial data to determine a parameter of statistical term of interest without suspending and while maintaining the blindness of said blinded ongoing clinical trial;

determine whether said parameter of statistical term of interest exceeds a threshold value and a difference in said parameter of statistical term of interest among said multi-arm study; and repeat the computer executable instructions for accessing said trial database, performing and determining during said blinded ongoing clinical trial and while maintaining the blindness of said blinded ongoing clinical trial until it is determined that said parameter of statistical term of interest exceeds said threshold value.

2. The computer readable storage medium of claim 1, further comprising computer executable instructions for receiving said threshold value selected by a user.

3. The computer readable storage medium of claim 1, wherein said parameter of statistical term of interest is a p-value; and further comprising computer executable instructions for determining whether the result of said statistical analysis exceeds a predetermined p-value.

4. The computer readable storage medium of claim 1, further comprising computer executable instructions for calculating a rate of change in said parameter of term of interest.

5. The computer readable storage medium of claim 4, further comprising computer executable instructions for determining whether said calculated rate of change in said parameter of statistical term of interest exceeds a threshold rate of change in said parameter of statistical term of interest.

6. The computer readable storage medium of claim 5, further comprising computer executable instructions for receiving said threshold rate of change in said parameter of statistical term of interest selected by a user.

7. The computer readable storage medium of claim 5, further comprising computer executable instructions for alerting a user if it is determined that said calculated rate of change in said parameter of statistical term of interest exceeds said threshold rate of change in said parameter of statistical term of interest.

8. The computer readable storage medium of claim 1, wherein said parameter of statistical term of interest is a p-value; and further comprising computer executable instructions for calculating a rate of change in said p-value.

9. The computer readable storage medium of claim 8, further comprising computer executable instructions for determining whether said calculated rate of change in said p-value exceeds a threshold rate of change in said p-value.

10. The computer readable storage medium of claim 8, further comprising computer executable instructions for alerting a user if it is determined that said calculated rate of change in said p-value exceeds said threshold rate of change in said p-value.

11. The computer readable storage medium of claim 1, further comprising computer executable instructions for determining whether said difference in said parameter of statistical term of interest among said multi-arm study exceeds a threshold difference in said parameter of statistical term of interest among said multi-arm study.

12. The computer readable storage medium of claim 11, further comprising computer executable instructions for alerting a user if it is determined that said difference in said parameter of statistical term of interest among said multi-arm study exceeds said threshold difference in said parameter of statistical term of interest among said multi-arm study.

13. The computer readable storage medium of claim 1, further comprising computer executable instructions for performing statistical analysis on said trial data to calculate said parameter of statistical term of interest without locking said trial database.

14. The computer readable storage medium of claim 1, further comprising computer executable instructions for waiting a predetermined time prior to repeating the steps of accessing, performing and determining during said ongoing clinical trial.

15. The computer readable storage medium of claim 1, wherein said ongoing clinical trial is a blinded ongoing clinical trial; and further comprising computer executable instructions for:

receiving a user defined criteria that defines a level of cleanliness of said parameter of statistical term of interest;

retrieving only those trial data satisfying said user defined criteria from said trial database.

16. The computer readable storage medium of claim 15, further comprising computer executable instructions for storing said grouped database in a memory device inaccessible by any user to preserve the blindness of said ongoing clinical trial.

17. The computer readable storage medium of claim 1, further comprising computer executable instructions for generating trends in said parameter of statistical term of interest over time.

18. The computer readable storage medium of claim 17, further comprising computer executable instructions for displaying said trends to an authorized user.

19. The computer readable storage medium of claim 17, further comprising computer executable instructions for predictive modeling of said trends to determine effects of altering study design of said ongoing clinical trial; wherein said study design comprises at least one of the following: length of said ongoing clinical trial, number of subjects enrolled in said ongoing clinical trial or distribution of enrolled subjects in said ongoing clinical trial.

20. A system for continuously analyzing trial data of an ongoing clinical trial, comprising:

a trial database comprising trial data of subjects in said ongoing clinical trial comprising a multi-arm study;

a blinding database comprising subject identifiers and associated study group identifiers, wherein a subject's study group being identifiable by a study group identifier; and a processor for:
  accessing said trial database to retrieve said trial data while maintaining blindness of said blinded ongoing clinical trial;
  accessing said blinded database to retrieve said subject identifiers and associated study group identifiers;
  generating a grouped database from said trial database and said blinded database for statistical analysis, said grouped database grouping said trial data of said subjects based on their study group;
  performing near real-time statistical analysis on said trial data to determine a parameter of statistical term of interest without suspending said ongoing clinical trial; and
  determining whether the result of said statistical analysis exceeds a threshold value;

wherein said processor is operable to repeatedly access, perform and determine during said ongoing clinical trial until it is determined that the result of said statistical analysis exceeds said threshold value.

21. The system of claim 20, wherein said processor is operable to receive said threshold value selected by a user.

22. The system of claim 20, wherein said parameter of statistical term of interest is a p-value; and wherein said processor is operable to determine whether said parameter of said statistical analysis exceeds a threshold p-value.

23. The system of claim 20, wherein said processor is operable to calculate a rate of change in said parameter of statistical term of interest.

24. The system of claim 23, wherein said processor is operable to determine whether said calculated rate of change in said parameter of statistical term of interest exceeds a threshold rate of change in said parameter of statistical term of interest.

25. The system of claim 24, wherein said processor is operable to receive said threshold rate of change in said parameter of statistical term of interest from a user.

26. The system of claim 24, wherein said processor is operable to alert a user if it is determined that said calculated rate of change in said parameter of statistical term of interest exceeds said threshold rate of change in said parameter of statistical term of interest.

27. The system of claim 20, wherein said parameter of statistical term of interest is a p-value; and wherein said processor is operable to calculate a rate of change in said p-value.

28. The system of claim 27, wherein said processor is operable to determine whether said calculated rate of change in said p-value exceeds a threshold rate of change in said p-value.

29. The system of claim 27, wherein said processor is operable to alert a user if it is determined that said calculated rate of change in said p-value exceeds said threshold rate of change in said p-value.

30. The system of claim 20, wherein said processor is operable to determine whether said difference in said parameter of statistical term of interest among said multi-arm study exceeds a threshold difference in said parameter of statistical term of interest among said multi-arm study.

31. The system of claim 30, wherein said processor is operable to alert a user if it is determined that said difference in said parameter of statistical term of interest among said multi-arm study exceeds said threshold difference in said parameter of statistical term of interest among said multi-arm study.

32. The system of claim 31, wherein said parameter of statistical term of interest is a p-value and a rate of change in the p-value.

33. The system of claim 20, wherein said processor is operable to wait a predetermined time prior to repeating the steps of accessing, performing and determining during and while maintaining the blindness of said ongoing clinical trial.

34. The system of claim 20, wherein said processor is operable to:
receive a user defined criteria that defines a level of cleanliness of said parameter of statistical term of interest;
retrieve only those trial data satisfying said user defined criteria from said trial database.

35. The system of claim 20, further comprising a memory device for storing said grouped database in a memory device inaccessible by any user to preserve the blindness of said ongoing clinical trial.

36. The system of claim 20, wherein said processor is operable to generate trends in said parameter of statistical term of interest over time.

37. The system of claim 36, further comprising a display for displaying said trends to an authorized user.

38. The system of claim 36, wherein said processor is operable to predictive model of said trends to determine effects of altering study design of said ongoing clinical trial; wherein said study design comprises at least one of the following: length of said ongoing clinical trial, number of subjects enrolled in said ongoing clinical trial or distribution of enrolled subjects in said ongoing clinical trial.

39. The system of claim 20, wherein said processor is operable to perform statistical analysis on said trial data to calculate said parameter of statistical term of interest without locking said trial database.

40. The computer readable media of claim 1, further comprising computer readable instructions for alerting a user if it is determined that the result of the statistical analysis exceeds said threshold value.

41. The system of claim 20, wherein said processor is operable to alert a user if it is determined that the result of the statistical analysis exceeds said threshold value.

* * * * *